United States Patent [19]
Konishi et al.

[11] Patent Number: 4,546,084
[45] Date of Patent: Oct. 8, 1985

[54] BIOLOGICALLY PURE CULTURE OF ACTINOMADURA SP.

[75] Inventors: Masataka Konishi, Kawasaki; Fumihide Sakai; Takeo Miyaki, both of Yokohama; Hiroshi Kawaguchi, Tokyo, all of Japan

[73] Assignee: Bristol-Myers Company, New York, N.Y.

[21] Appl. No.: 598,114

[22] Filed: Apr. 9, 1984

Related U.S. Application Data

[62] Division of Ser. No. 401,468, Jul. 26, 1982.

[51] Int. Cl.[4] .................. C12N 1/20; C12P 21/00; C12R 1/03
[52] U.S. Cl. ...................... 435/253; 435/68; 435/825
[58] Field of Search .............. 435/68, 70, 71, 75, 435/243, 253, 170, 825, 872

[56] References Cited

U.S. PATENT DOCUMENTS

| | | | |
|---|---|---|---|
| 3,334,022 | 8/1967 | Ishida et al. | 424/116 |
| 3,595,954 | 7/1971 | Umezawa et al. | 424/117 |
| 4,148,882 | 4/1979 | Celmer et al. | 424/122 |

OTHER PUBLICATIONS

J. Antibiotics 18: 68–76, (1965), Ishida et al.
Cancer Treatment Reviews 6: 239–249, (1979), Issell et al.
J. Antibiotics 21: 44–49, (1968), Chimura et al.
J. Antibiotics 29: 415–423, (1976), Yamashita et al.
J. Antibiotics 32: 330–339, (1979), Yamashita et al.

Primary Examiner—Thomas G. Wiseman
Assistant Examiner—Jean A. Heck
Attorney, Agent, or Firm—David M. Morse

[57] ABSTRACT

A biologically pure culture of Actinomadura Sp. Strain H710-49 (ATCC 39144) is provided. The antibiotic designated BBM-1644 may be produced by fermentation of the subject culture.

1 Claim, 2 Drawing Figures

IR SPECTRUM OF BBM-1644 (in KBr)

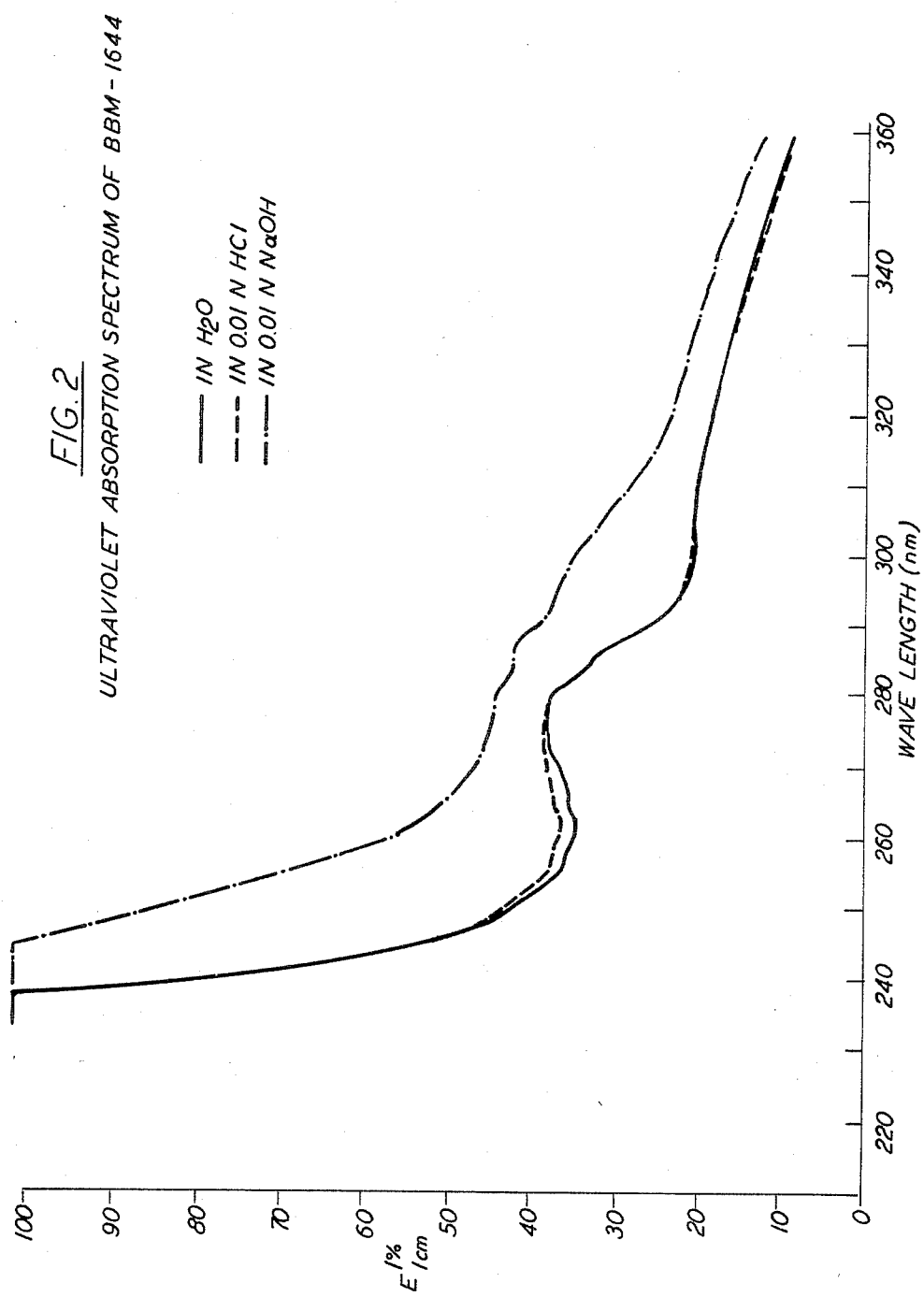

4,546,084

BIOLOGICALLY PURE CULTURE OF ACTINOMADURA SP.

This is a division of application Ser. No. 401,468 filed July 26, 1982.

BACKGROUND OF THE INVENTION (1) Field of the Invention

This invention relates to a new antitumor antibiotic and to its production and recovery.

(2) Description of the Prior Art

The antitumor antibiotic of the present invention, BBM-1644, is a new member of the protein antitumor antibiotics exemplified by neocarzinostatin, macromomycin and auromoycin.

Neocarzinostatin (also called zinostatin) is an acidic protein macromolecule of molecular weight 10,700 consisting of a single polypeptide chain of 109 amino acids cross-linked by two disulfide bridges. Production of neocarzinostatin by fermentation of strains of *Streptomyces carzinostaticus* var. *neocarzinostaticus* is disclosed in U.S. Pat. No. 3,334,022 and in *J. Antibiotics* 18: 68–76 (1965). The amino acid sequence of neocarzinostatin is disclosed in *Cancer Treatment Reviews* 6: 239–249 (1979).

Macromomycin is a neutral or weakly acidic polypeptide with an approximate molecular weight of about 15,000. Production of macromomycin by fermentation of *Streptomyces macromomyceticus* (NIHJ MC-8-42) is disclosed in U.S. Pat. No. 3,595,954 and in *J. Antibiotics* 21: 44–49 (1968). *Purification of macromomycin* and characterization data for the purified compound are disclosed in *J. Antibiotics* 29: 415–423 (1976).

Auromomycin is a weakly acidic polypeptide with a molecular weight of about 12,500 and an isoelectric point of pH 5.4. It consists of 16 different amino acids. Isolation of auromomycin from the culture broth of *Streptomyces macromomyceticus* and characterizing properties of the purified product are disclosed in *J. Antibiotics* 32: 330–339 (1979).

BBM-1644 may be differentiated from known polypeptide antitumor antibiotics such as neocarzinostatin, macromomycin and auromomycin by physico-chemical properties such as molecular weight, amino acid content and paper electrophoresis.

SUMMARY OF THE INVENTION

There is provided by the present invention a new protein antitumor antibiotic designated herein as BBM-1644, said antibiotic being prepared by cultivating a new strain of Actinomadura designated Actinomadura sp. strain H710-49 (ATCC 39144) in an aqueous nutrient medium containing assimilable sources of carbon and nitrogen under submerged aerobic conditions until a substantial amount of BBM-1644 is produced by said organism in said culture medium and optionally recovering the BBM-1644 from the culture medium. The invention embraces the BBM-1644 antibiotic in dilute solution, as a crude concentrate, as a crude solid and as a purified solid.

DESCRIPTION OF THE DRAWINGS

FIG. 2 shows the ultraviolet absorption spectra of BBM-1644 in water, 0.01N HCl and 0.01N NaOH.

DETAILED DESCRIPTION

Figure 1:
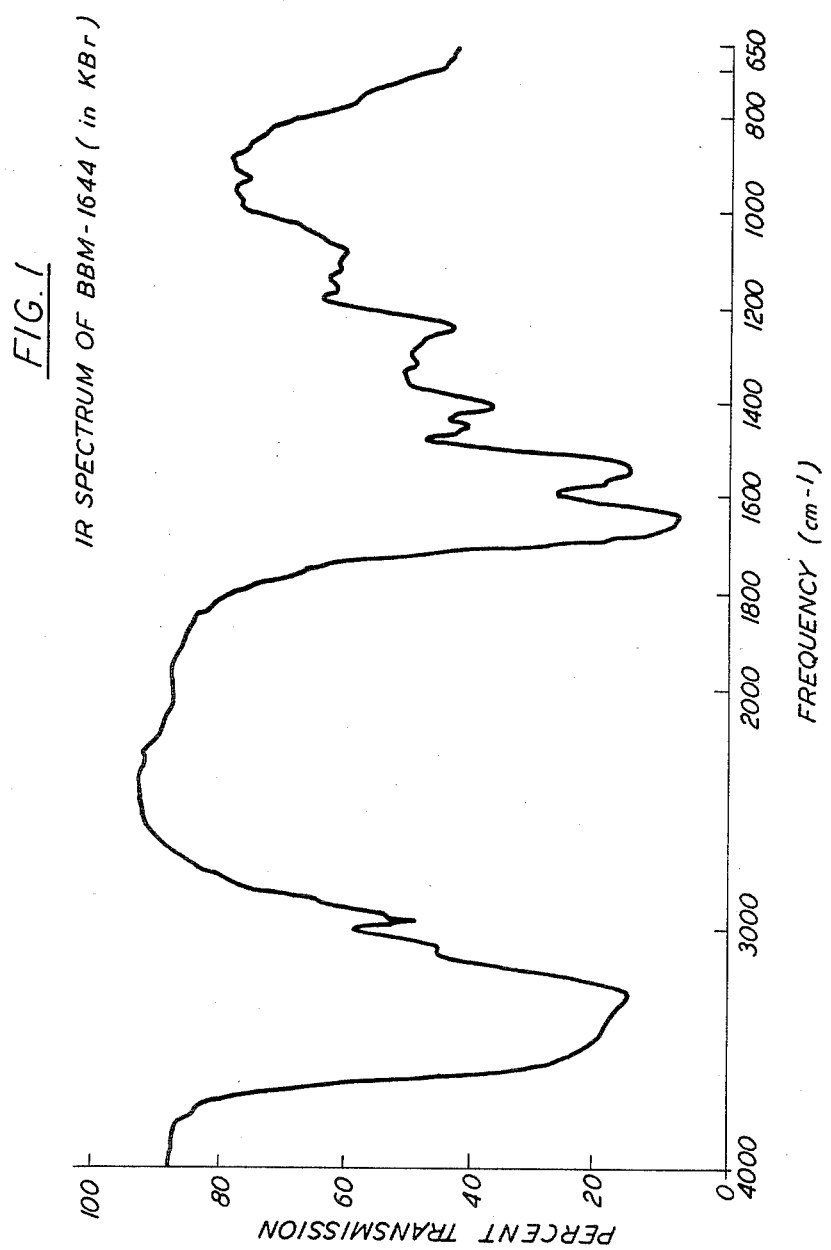
FIG. 1 shows the infrared absorption spectrum of BBM-1644 (KBr pellet).

This invention relates to a novel protein antitumor antibiotic designated herein as BBM-1644 and to its preparation by fermentation of a new strain of Actinomadura designated Actinomadura sp. strain H710-. The above organism was isolated from a soil sample collected in West Germany. A biologically pure culture of the organism has been deposited with the American Type Culture Collection, Washington, D.C., and added to its permanent collection of microorganisms as ATCC 39144.

BBM-1644 inhibits the growth of various gram-positive and acid-fast bacteria. The antibiotic also exhibits phage inducing properties in lysogenic bacteria and inhibits growth of lymphatic and solid tumors such as P388 leukemia in mice. The new antibiotic, therefore, may be used as an antibacterial agent or as an antitumor agent for inhibiting mammalian tumors.

The Microorganism

The actinomycete strain No. H710-49 was isolated from a soil sample and prepared by conventional procedures as a biologically pure culture for characterization. Strain H710-49 forms both substrate and aerial mycelia. The substrate mycelium is long, branched and not fragmented into short filaments. Short spore-chains are born on the tip or monopodial branch of aerial mycelium. The spore-chains contain 2 to 15 spores in a chain (mostley 4 8 spores) and are straight, hooked or looped in shape. The spores have a warty surface and are oval to elliptical (0.5~0.6 ×0.7~1.2μm) in shape with a round or pointed end. Mature spores are often separated by empty hyphae. Terminal swellings of hyphae are occasionally observed on the substrate mycelium in Czapek's agar and Bennett's agar. Motile spores, sporangia or sclerotic granules are not seen in any media examined.

Unlike ordinary species of the genus Streptomyces, strain H710-49 grows slowly and forms poor aerial mycelium in chemically defined media and natural organic media. The color of aerial mycelium is white and turns to a pinkish shade after sporulation in oatmeal agar, inorganic salts-starch agar and glycerol-asparagine agar. Mass color of the substrate mycelium is colorless, yellow, reddish brown or dark grayish brown. Melanoid pigment is not produced, but a lemon yellow diffusible pigment is seen in glycerolasparagine agar, tyrosine agar and Pridham-Gottlieb's basal agar supplemented with any one of glycerol, L-arabinose, D-xylose, L-rhamnose, D-glucose, D-fructose, trehalose and D-mannitol. Strain H710-49 grows at 20° C., 28° C. and 37° C., but not at 10° C. or 41° C. It is sensitive to NaCl at 10% but not at 7%, and resistant to lysozyme at 0.001%. D-Galactose, D-mannose, sucrose, raffinose and inositol are not utilized by the strain. Cultural and physiological characteristics of strain H710-49 are shown in Tables 1 and 2, respectively. The pattern of carbon source utilization by the strain is shown in Table 3.

TABLE 1

| Cultural characteristics* of strain H710-49 | | |
|---|---|---|
| Tryptone-yeast extract broth (ISP No. 1) | G** | poor to moderate; floccose, sedimented and not pigmented. |
| Sucrose-nitrate agar (Czapek's agar) | G | scant |
|  | R | colorless to pale orange yellow (73)*** |
|  | A | scant; white (263) |

TABLE 1-continued

Cultural characteristics* of strain H710-49

| | | |
|---|---|---|
| Glucose-asparagine agar | D | none |
| | G | poor |
| | R | yellowish white (92) to deep orange yellow (69) |
| | A | very scant; white (263) |
| | D | none |
| Glycerol-asparagine agar (ISP No. 5) | G | poor to moderate |
| | R | pale yellow (89) to dark orange yellow (72) |
| | A | poor; white (263) to pale yellowish pink (31) |
| | D | brilliant yellow (83) |
| Inorganic salts-starch agar (ISP No. 4) | G | poor to moderate |
| | R | colorless to deep yellow (85) |
| | A | poor; pinkish white (9) to pale yellowish pink (31) |
| | D | none |
| Tyrosine agar (ISP No. 7) | G | moderate |
| | R | brownish orange (54) to moderate reddish brown (43) |
| | A | poor; white (263) to pale yellow (89) |
| | D | strong yellow (84) |
| Nutrient agar | G | poor to moderate |
| | R | yellowish white (92) to moderate yellowish brown (77) |
| | A | poor; white (263) |
| | D | none |
| Yeast extract-malt extract agar (ISP No. 2) | G | moderate |
| | R | dark yellow (88) to dark brown (59) |
| | A | scant; white (263) |
| | D | light olive brown (94) |
| Oatmeal agar (ISP No. 3) | G | poor |
| | R | colorless |
| | A | poor; white (263) to pinkish white (9) |
| | D | none |
| Bennett's agar | G | moderate |
| | R | grayish yellowish brown (80) to dark grayish brown (62) |
| | A | very scant; white (263) |
| | D | moderate olive brown (95) |
| Peptone-yeast extract-iron agar (ISP No. 6) | G | poor |
| | R | grayish yellow (90) to dark grayish brown (62) |
| | A | poor; white (263) |
| | D | none to moderate yellowish brown (77) |

*observed after incubation at 28° C. for 3 weeks
**Abbreviation: G — Growth; R — Reverse Color; A — Aerial mycelium; D — Diffusible pigment
***Color and number in parenthesis follow the color standard in "Kelly, K. L. & D. B. Judd: ISCC-NBS color-name charts illustrated with Centroid Colors. U.S. Dept. of Comm. Circ. 553, Washington, D.C., Nov., 1975"

TABLE 2

Physiological characteristics of strain H710-49

| Test | Response | Method and medium |
|---|---|---|
| Range of temperature for growth | Maximal growth at 28° C. Moderate growth at 20° C. and 37° C. No growth at 10° C. and 41° C. | Bennett's agar |
| Gelatin liquefaction | Liquefied | Glucose-peptone-gelatin medium |
| Starch hydrolysis | Hydrolyzed | Starch agar plate |
| Reactions in skimmed milk | Not coagulated and completely peptonized | Difco skimmed milk |
| Formation of melanoid | Not produced | Tryptone-yeast extract broth, tyrosine agar and peptone-yeast extract-iron agar |
| Nitrate reduction | Reduced | Czapek's glucose-nitrate broth and glucose-yeast extract-nitrate broth |
| Resistance to NaCl | Moderately resistant. Growth at 7% but not at 10%. | Tryptone-yeast extract agar |
| Lysozyme | Resistant. Growth at 0.001%. | Tryptone-yeast extract agar |
| pH | Growth at 6.0 but not at 5.0. | Tryptone-yeast extract agar |

TABLE 3

Utilization of carbon sources* by strain H710-49

| | |
|---|---|
| Glycerol | + |
| D(−)-Arabinose | − |
| L(+)-Arabinose | + |
| D-Xylose | + |
| D-Ribose | + |
| L-Rhamnose | + |
| D-Glucose | + |
| D-Galactose | − |
| D-Fructose | + |
| D-Mannose | − |
| L(−)-Sorbose | − |
| Sucrose | − |
| Lactose | − |
| Cellobiose | + |
| Melibiose | − |
| Trehalose | + |
| Raffinose | − |
| D(+)-Melezitose | − |
| Soluble starch | ± |
| Cellulose | − |
| Dulcitol | − |
| Inositol | − |
| D-Mannitol | + |
| D-Sorbitol | − |
| Salicin | − |

*Observed after incubation at 28° C. for 3 weeks.
Basal medium: Pridham-Gottlieb inorganic medium Purified cell-wall of strain H710-49 contains mesodiaminopimelic acid but lacks glycine. The whole cell hydrolyzate shows the presence of madurose (3-O-methyl-D-galactose), glucose, ribose and a small amount of mannose. The cell-wall composition and whole cell sugar components of strain H710-49 indicate that the strain belongs to cell-wall Type III$_B$.

The above-described characteristics of strain H710-49 resemble those of the genus Actinomadura. According to the numerical taxonomy of Actinomadura and related actinomycetes by Goodfellow et al. in *J. Gen. Microbiol.* 112: 95–111 (1979), most Actinomadura species of soil origin are classified into Cluster No. 7 among the 14 clusters described. Strain No. H710-49 is most related to the species of Cluster 7. Nonomura and Ohara in *J. Ferment. Technol.* 49: 904–912 (1971) reported five saprophytic species of the genus Actinomadura and Nonomura [*J. Ferment. Technol.* 52: 71–77 (1974)] and Preobrazhenskaya et al. [*Actinomycetes and Related Organisms* 12: 30–38 (1977)] described the identification and classification of Actinomadura species. As a result of comparison with known Actinomadura species described in the literature, strain H710-49 is considered to belong to a new species of Actinomadura similar to *A. roseola, A. salmonea, A. vinacea* or *A. corallina* described in the Preobrazhenskaya et al. reference above and in Japanese Kokai 55/94391.

It is to be understood that for the production of BBM-1644, the present invention, though described in detail with reference to the particular strain Actinomadura sp. strain H710-49 (ATCC 39144), is not limited to this microorganism or to microorganisms fully described by the cultural characteristics disclosed herein. It is specifically intended that the invention embrace strain H710-49 and all natural and artificial BBM-1644-producing variants and mutants thereof.

Antibiotic Production

The BBM-1644 antibiotic of the present invention may be prepared by cultivating a BBM-1644-producing strain of the genus Actinomadura, preferably a strain of Actinomadura sp. having the identifying characteristics of ATCC 39144 or a mutant thereof, in a conventional aqueous nutrient medium. The organism is grown in a nutrient medium containing known nutritional sources for actinomycetes, i.e. assimilable sources of carbon and nitrogen plus optional inorganic salts and other known growth factors. Submerged aerobic conditions are preferably employed for the production of large quantities of antibiotic, although for production of limited amounts, surface cultures and bottles may also be used. The general procedures used for the cultivation of other actinomycetes are applicable to the present invention.

The nutrient medium should contain an appropriate assimilable carbon source such as glycerol, L(+)-arabinose, D-xylose, D-ribose, D-glucose, D-fructose, soluble starch, D-mannitol or cellobiose. As nitrogen sources, ammonium chloride, ammonium sulfate, urea, ammonium nitrate, sodium nitrate, etc. may be used either alone or in combination with organic nitrogen sources such as peptone, meat extract, yeast extract, corn steep liquor, soybean powder, cotton seed flour, etc. There may also be added if necessary nutrient inorganic salts to provide sources of sodium, potassium, calcium, ammonium, phosphate, sulfate, chloride, bromide, carbonate, zinc, magnesium, manganese, cobalt, iron, and the like.

Production of the BBM-1644 antibiotic can be effected at any temperature conducive to satisfactory growth of the producing organism, e.g. 20°–37° C., and is conveniently carried out at a temperature of around 27°–32° C. Ordinarily, optimum production is obtained in shaker flasks after incubation periods of about 6–7 days. When tank fermentation is to be carried out, it is desirable to produce a vegetative inoculum in a nutrient broth by inoculating the broth culture with a slant or soil culture or a lyophilized culture of the organism. After obtaining an active inoculum in this manner, it is transferred aseptically to the fermentation tank medium. Antibiotic production may be monitored by the paper disc-agar diffusion assay using *Bacillus subtilis* M45 [Rec$^-$ mutant; *Mutation Res.* 16: 165–174 (1972)] as the test organism.

Isolation and Purification

When fermentation is complete, BBM-1644 exists mainly in the liquid part of the fermented broth after separation of the solid part by filtration or centrifugation. Thus, the harvested broth may be separated into mycelial cake and broth supernatant by centrifugation. The filtrate is then concentrated and dialyzed against tap water by a semipermeable membrane such as a cellophane tube to remove permeable impurities. The inside-retained solution (after removal of insoluble materials) containing the BBM-1644 may then be saturated with a salting out reagent such as ammonium sulfate to precipitate out BBM-1644 as a crude solid. This solid may be dissolved in water and desalted by dialysis against tap water.

Further purification of the crude BBM-1644 may be accomplished by conventional procedures used with other acidic polypeptides. For example, the aqueous solution containing BBM-1644 may be adsorbed on an ion exchanger such as DEAE-Sephadex, DEAE-Cellulose, CM-Sephadex or CM-cellulose and eluted with a neutral salt solution. Successive chromatographic steps are preferably employed with a gradient concentration of salt solution used as the eluant. Aqueous fractions containing the purified BBM-1644 are then concentrated to dryness as by lyophilization.

Physico-chemical Properties of BBM-1644

BBM-1644 is isolated as an amorphous white powder upon lyophilization. When examined by high voltage paper electrophoresis (4500 V in 0.05M barbital buffer at pH 8.6), BBM-1644 migrates as an acid travelling 8.7 cm toward the anode after one hour. BBM-1644 does not show a definite melting point and gradually decomposes above 240° C. It is soluble in water, but practically insoluble in common organic solvents such as methanol, ethanol, acetone, ethyl acetate and n-hexane. The antibiotic shows an optical rotation of $[\alpha]_D^{26} = -75.6°$ in 0.25% aqueous solution. As depicted in FIG. 2, the UV spectrum of BBM-1644 shows absorption maxima at 275 nm ($E_{1\ cm}^{1\%}$8.2) and 310 nm ($E_{1\ cm}^{1\%}$4.6, shoulder) in aqueous solution. It exhibits a nearly identical UV spectrum in water and in 0.01N HCl solution, but only a single maximum at 285 nm ($E_{1\ cm}^{1\%}$8.9) in 0.01N NaOH solution. The IR spectrum of BBM-1644 measured in KBr is shown in FIG. 1. The spectrum indicates the presence of NH and OH groups (3300~2980 cm$^{-1}$) and amide groups (1650 and 1540 cm$^{-1}$). The antibiotic gives positive reactions to Folin-Lowry, xanthoprotein, biuret and ninhydrin reagents and decolorizes potassium permanganate solution. It is negative to anthrone and Sakaguchi reactions. When co-chromatographed on Sephadex G-75 with ovalbumin (MW 43,000), chymotrypsinogen (25,000) and ribonuclease A (13,700), BBM-1644 is eluted just after chymotrypsinogen and therefore its molecular weight is estimated to be around 22,000. Elemental analysis of BBM-1644 indicates carbon 46.60%, hydrogen 6.45%, nitrogen 13.34% and sulfur 0.20%. The presence of 13 kinds of amino acids in the BBM-1644 molecule was revealed by amino acid analysis as shown in Table 4. Basic amino acids such as lysine, histidine and arginine are not present in BBM-1644.

TABLE 4

Amino acid composition of BBM-1644

| Amino acid | Relative composition* of amino acids |
|---|---|
| Alanine | 8.8 |
| Aspartic acid | 6.0 |
| half-Cystine | 1.0 |
| Glutamic acid | 5.7 |
| Glycine | 8.7 |
| Isoleucine | 2.3 |
| Leucine | 1.0 |
| Phenylalanine | 1.4 |
| Proline | 4.1 |
| Serine | 1.6 |
| Threonine | 7.2 |
| Tyrosine | 0.6 |
| Valine | 11.1 |

*Content of leucine was arbitrarily assigned as 1.0.

BBM-1644 is fairly stable in the pH range of 2~9, but the stability declines sharply beyond this pH range. The aqueous solution of BBM-1644 is stable for 2 hours at 50° C. at neutral pH. Upon exposure to ultraviolet light, the antibiotic activity of BBM-1644 is lost within 20 minutes.

The physico-chemical properties of BBM-1644 described above indicate that it is a member of the protein antitumor antibiotic group which includes neocarzinostatin, macromomycin and auromomycin. BBM-1644, however, can be differentiated from the known protein antitumor antibiotics by its molecular weight, amino acid content and paper electrophoresis. The paper electrophoretic mobilities of BBM-1644, neocarzinostatin and macromomycin are shown in Table 5.

TABLE 5

| | Paper electrophoresis* Mobility (mm from the loading spot) |
|---|---|
| BBM-1644 | +87 |
| Neocarzinostatin | +31 |
| Macromomycin | −20 |

*4,500 V. 1 hour; Barbital buffer pH 8.6

The neocarzinostatin group of antibiotics commonly exhibit two UV absorption maxima at around 275 and 350 nm, while BBM-1644 has the UV maxima at around 275 and 310 nm. It has recently been reported in *Biochem. Res. Commun.* 95: 1351–1356 (1980) that the maximum at 350 nm of the neocarzinostatin antibiotics might be due to the non-protein chromophores which are essential for their biological activity. It is noted that BBM-1644 has a chromophore different from that of the known neocarzinostatin group of antibiotics.

Biological Properties of BBM-1644

The antibacterial activity of BBM-1644 was determined by the serial two-fold agar dilution method. Nutrient agar medium was used for gram-positive and gram-negative bacteria; nutrient agar medium containing 4% glycerol for acid-fast bacteria and Sabaouraud agar medium for fungi. The activity was expressed as minimum inhibitory concentration (MIC) in the agar medium and the results are shown in Table 6 along with those of neocarzinostatin. BBM-1644 showed potent inhibitory activity against gram-positive and acid-fast bacteria but did not inhibit the growth of gram-negative bacteria and fungi. The antibacterial spectrum of BBM-1644 is similar to that of neocarzinostatin, while the intrinsic activity of BBM-1644 is more potent than the latter in some of the test organisms.

TABLE 6

In vitro antimicrobial activity

| | MIC in mcg/ml | |
|---|---|---|
| Test organism | BBM-1644 | Neocarzinostatin |
| *Staphylococcus aureus* FDA 209P | 0.4 | 1.6 |
| *Staphylococcus aureus* Smith | 0.2 | 0.8 |
| *Streptococcus pyogenes* A20201 | 6.3 | 3.1 |
| *Micrococcus luteus* PCI 1001 | 1.6 | 1.6 |
| *Micrococcus flavus* D12 | 1.6 | 1.6 |
| *Bacillus subtilis* PCI 219 | 0.8 | 3.1 |
| *Escherichia coli* NIHJ | >100 | >100 |
| *Klebsiella pneumoniae* D-11 | >100 | >100 |
| *Proteus vulgaris* A9436 | >100 | >100 |
| *Pseudomonas aeruginosa* A9930 | >100 | >100 |
| *Mycobacterium smegmatis* 607 D87 | 12.5 | 50 |
| *Mycobacterium phlei* D88 | 3.1 | 12.5 |
| *Candida albicans* IAM 4888 | >100 | >100 |

The ability of BBM-1644 to induce prophage in lysogenic bacterium (ILB) was determined by the method of Lein et. al. (*Nature* 196: 783–784, 1962) using neocarzinostatin as a reference compound. The plaque count was made on agar plates containing test material (T) and control (C). A T/C ratio of the plaque counts of greater than 3 was considered significant and the ILB activity was expressed by the minimum inducing concentration of the test compound. As shown in Table 7, the ILB activity of BBM-1644 is similar to that observed with neocarzinostatin, the minimum inducing concentration being 1 mcg/ml.

TABLE 7

Induction of lysogenic bacterium by BBM-1644

| | ILB activity (T/C)* | | | |
|---|---|---|---|---|
| | 100 | 10 | 1 | 0.1 mcg/ml |
| BBM-1644 | 10.4 | 10.3 | 6.0 | 1.2 |
| Neocarzinostatin | 28.6 | 20.4 | 10.8 | 0.7 |

*significant activity: T/C of >3.0

The antitumor activity of BBM-1644 was determined in mice ($BDF_1$ strain) against lymphocytic leukemia P388. Each mouse was inoculated intraperitoneally with $3 \times 10^5$ cells of the tumor. Graded doses of the antibiotic were administered to mice intraperitoneally 24 hours after tumor implantation. The treatments were given once a day on days 1, 4 and 7 (q3d ×3 schedule) or 9 consecutive days (qd 1→9 schedule). Neocarzinostatin was comparatively tested as a reference antitumor agent and the results are summarized in Table 8. BBM-1644 was highly active against the mouse leukemia in a dose range of 0.03~1.0 mg/kg/day by both treatments. The antitumor activity of BBM-1644 was about the same as (qd 1→9 schedule) or 3 times more potent (q3d×3 schedule) than that of neocarzinostatin in terms of minimun effective dose.

TABLE 8

Antitumor activity against leukemia P388

| | T/C (%) in MST* Dose in mg/kg/day, ip, q3d × 3 | | | | |
|---|---|---|---|---|---|
| | 1 | 0.3 | 0.1 | 0.03 | 0.01 |
| BBM-1644 | 188 | 188 | 138 | 125 | 113 |
| Neocarzinostatin | 163 | 150 | 125 | 113 | |

T/C (%) in MST
Dose in mg/kg/day, ip, gd 1→9

TABLE 8-continued

| Antitumor activity against leukemia P388 | | | | |
|---|---|---|---|---|
| | 0.3 | 0.1 | 0.03 | 0.01 |
| BBM-1644 | 125 | 175 | 138 | 113 |
| Neocarzinostatin | 163 | 138 | 125 | 113 |

*median survival time; significant activity: T/C of ≧125%

Antitumor activity of BBM-1644 was also indicated by a second test against P388 leukemia in mice, the results of which are shown below in Table 9. Details of the methods used in this test have been described in *Cancer Chemother. Rep.* 3: 1-87 (Part 3), 1972.

TABLE 9

Effect of BBM-1644 on P388 Leukemia

| Material | Treatment Schedule | Dose, IP mg/kg/inj | MST Days | Effect MST % T/C | AWC gm d.6 | Survivors Day 5 (30) |
|---|---|---|---|---|---|---|
| Neo-carzinostatin | D.1,4&7 | 1.6 | 8.0 | 89 | −4.8 | 6/6 |
| | | 0.8 | 10.5 | 117 | −4.3 | 6/6 |
| | | 0.4 | 15.5 | 172 | −3.2 | 6/6 |
| | | 0.2 | 15.0 | 167 | −2.5 | 6/6 |
| | | 0.1 | 13.5 | 150 | −1.2 | 6/6 |
| | | 0.05 | 12.0 | 133 | −1.7 | 6/6 |
| BBM-1644 | D.1 | 2.56 | 9.0 | 100 | — | 4/6 |
| | | 1.28 | 14.0 | 156 | −4.1 | 6/6 |
| | | 0.64 | 14.5 | 161 | −4.9 | 6/6 |
| | | 0.32 | 16.5 | 183 | −4.8 | 6/6 |
| | | 0.16 | 14.0 | 156 | −4.1 | 6/6 |
| | | 0.08 | 12.0 | 133 | −2.8 | 6/6 |
| | | 0.04 | 10.5 | 117 | −2.7 | 6/6 |
| | | 0.02 | 11.0 | 122 | −2.5 | 6/6 |
| | D.1,4&7 | 1.28 | 23.5 | 261 | −3.3 | 6/6 |
| | | 0.64 | 19.0 | 211 | −3.5 | 6/6 |
| | | 0.32 | 18.5 | 206 | −4.3 | 6/6 |
| | | 0.16 | 14.5 | 161 | −3.8 | 6/6 |
| | | 0.08 | 12.0 | 133 | −3.3 | 6/6 |
| | | 0.04 | 12.0 | 133 | −2.9 | 6/6 |
| | | 0.02 | 10.0 | 111 | −2.5 | 6/6 |
| | | 0.01 | 10.0 | 111 | −1.9 | 6/6 |
| | QD 1→9 | 0.64 | 8.0 | 89 | −5.2 | 6/6 |
| | | 0.32 | 10.0 | 111 | −4.2 | 6/6 |
| | | 0.16 | 19.0 | 211 | −4.3 | 6/6 |
| | | 0.08 | 18.0 | 200 | −4.2 | 6/6 |
| | | 0.04 | 15.5 | 172 | −3.5 | 6/6 |
| | | 0.02 | 13.0 | 144 | −3.3 | 6/6 |
| | | 0.01 | 12.0 | 133 | −2.2 | 6/6 |
| Control | $10^7$ | Saline | 8.0 | — | — | 10/10 |
| | $10^6$ | Saline | 9.0 | — | −0.3 | 20/20 |
| | $10^5$ | Saline | 11.0 | — | — | 10/10 |
| | $10^4$ | Saline | 14.0 | — | — | 10/10 |

Tumor inoculum: $10^6$ ascites cells, ip (plus titration)
Host: CDF₁ ♀ mice.
Tox: <4/6 mice alive on Day 5.
Evaluation: MST = median survival time.
Effect: % T/C = (MST treated/MST control) × 100.
Criteria: % T/C ≧ 125 considered significant antitumor activity The acute toxicity of BBM-1644 was determined in mice (dd Y strain) by single intraperitoneal administration, the LD$_{50}$ being calculated as 5.8 mg/kg.

As shown above, BBM-1644 possesses potent antibacterial activity against gram-positive and acid-fast bacteria and is thus useful in the therapeutic treatment of mammals and other animals for infectious diseases caused by such bacteria. Additionally, it may be utilized for other conventional applications of antibacterial agents such as disinfecting medical and dental equipment.

The induction of phophage in lysogenic bacteria and the marked antitumor activity shown against P388 leukemia in mice indicate that BBM-1644 is also therapeutically useful in inhibiting the growth of mammalian tumors.

The present invention, therefore, provides a method for therapeutically treating an animal host affected by a bacterial infection or by a malignant tumor which comprises administering to said host an effective antibacterial or tumor-inhibiting dose of BBM-1644 or a pharmaceutical composition thereof.

In another aspect, the present invention provides a pharmaceutical composition which comprises an effective antibacterial or tumor-inhibiting amount of BBM-1644 in combination with an inert pharmaceutically acceptable carrier or diluent. These compositions may be made up in any pharmaceutical form appropriate for parenteral administration.

Preparations according to the invention for parenteral administration include sterile aqueous or non-aqueous solutions, suspensions or emulsions. They may also be manufactured in the form of sterile solid compositions which can be dissolved in sterile water, physiological saline or some other sterile injectable medium immediately before use.

It will be appreciated that the actual preferred amounts of the BBM-1644 antibiotic used will vary according to the particular composition formulated, the mode of application and the particular situs, host and disease being treated. Many factors that modify the action of the drug will be taken into account by those skilled in the art, for example, age, body weight, sex, diet, time of administration, route of administration, rate of excretion, condition of the host, drug combinations, reaction sensitivities and severity of the disease. Administration can be carried out continuously or periodically within the maximum tolerated dose. Optimal application rates for a given set of conditions can be ascertained by those skilled in the art using conventional dosage determination tests in view of the above guidelines.

The following examples are provided for illustrative purposes only and are not intended to limit the scope of the invention. DEAE Cellulose is a diethylaminoethyl ion exchange cellulose. SEPHADEX G-50 is a filtration gel manufactured by Pharmacia Fine Chemicals, Inc. DEAE SEPHADEX A-50 is a diethylaminoethyl anion exchange gel manufactured by Pharmacia Fine Chemicals, Inc. SEPHADEX® is a trademark of Pharmacia Fine Chemicals, Inc.

EXAMPLE 1

Fermentation of BBM-1644

An agar slant with well established growth of Actinomadura sp. H710-49 was used to inoculate seed medium (100 ml in a 500-ml Erlenmyer flask) containing 1% mannitol, 2% peptone and 1% yeast extract, the pH being adjusted to 7.2 before sterilization. The seed culture was incubated at 32° C. for 72 hours on a rotary shaker (250 rpm) and 5 ml of the culture was transferred to the second seed medium (100 ml) composed of the same composition as the first seed medium. It was cultivated under the same condition as that used for the first seed culture. Five ml of the inoculum growth thus prepared was employed to start fermentation in 500-ml Erlenmyer flasks which contained 100 ml of fermentation medium having composition of 2.5% mannitol, 0.5% glucose, 1% soybean meal, 0.5% peptone, 1% meat extract, 0.3% CaCO$_3$ and 0.2% NaCl. Fermentation was carried out at 28° C. on a rotary shaker with 250 rpm rotation. The antibiotic production was monitored by the paper disc-agar diffusion assay using *Bacillus subtilis* M45 (Rec⁻ mutant) as the test organism. The antibiotic activity in the culture broth gradually increased with the progress of fermentation and reached about 300 mcg/ml after 6~7 days.

EXAMPLE 2

The harvested broth (18 liters) obtained from the Example 1 fermentation was separated to mycelial cake and broth supernatant by using a sharpless centrifuge apparatus (Kokusan No. 4A). The filtrate was concentrated below 40° C. to one-tenth the original volume and the concentrate was dialyzed by cellophane tubing (Union Carbide) against tap water in a cold room. The inside-retained solution was concentrated to about 1.5 liters which was centrifuged (8,000 G) to remove insoluble materials. The clear supernatant was saturated with ammonium sulfate and allowed to stand for 5 hours at 5° C. The precipitate formed was collected by centrifugation, dissolved in water (300 ml) and desalted by dialysis against tap water. The dialyzed solution (700 ml) contained 22 grams of crude solid of BBM-1644 as revealed by lyophilization of a part of the solution. The rest of the solution was used for subsequent purification without concentration in order to avoid decomposition. The antibiotic solution was passed through a column of DEAE-cellulose (Cl⁻, 400 ml) and the column was washed with water (1 liter) and developed with 1/15M phosphate buffer (pH 7.0) containing 0.3M sodium chloride. The active fractions were combined (300 ml), dialyzed for 18 hours against tap water and chromatographed on a column of DEAE-cellulose (400 ml) which had been equilibrated with 1/15M phosphate buffer (pH 7.5). The column was developed with the same buffer solution containing an increasing amount of sodium chloride (0~0.2M). The active eluate was desalted by dialysis and charged on a column of DEAE-Sephadex A-50 (17 ml). The column was developed with 1/15M phosphate buffer (pH 7.5) containing a gradient concentration of sodium chloride (0~0.3M). The active fractions as determined by *B. subtilis* M45 assay were pooled and dialyzed against running water for 18 hours. The desalted solution was chromatographed on a column of DEAE-Sephadex A-50 (18 ml) using a 1/15M phosphate buffer (pH 7.0)-NaCl (0~0.3M) system as an eluant. The appropriate fractions were collected, concentrated to 10 ml and applied on a column of Sephadex G-50 for desalting. The column was eluted by deionized water and the active eluate lyophilized to afford 120 mg of white powder. The sample of BBM-1644 thus obtained was homogeneous as revealed by polyacrylamide gel electrophoresis.

We claim:

1. A biologically pure culture of the microorganism Actinomadura sp. ATCC 39144, said culture being capable of producing the antibiotic BBM-1644 in a recoverable quantity upon cultivation in an aqueous nutrient medium containing assimilable sources of nitrogen and carbon.

* * * * *